(12) United States Patent  
Ruocco et al.

(10) Patent No.: US 8,505,360 B2  
(45) Date of Patent: Aug. 13, 2013

(54) BREATH SAMPLING METHODOLOGY HAVING IMPROVED RELIABILITY

(75) Inventors: John T. Ruocco, Mastic, NY (US); Ronald A. Koppel, Ronkonkoma, NY (US)

(73) Assignee: Interceptor Ignition Interlocks Inc., Pawling, NY (US)

( * ) Notice: Subject to any disclaimer, the term of this patent is extended or adjusted under 35 U.S.C. 154(b) by 256 days.

(21) Appl. No.: 12/852,693

(22) Filed: Aug. 9, 2010

(65) Prior Publication Data

US 2012/0031165 A1    Feb. 9, 2012

(51) Int. Cl.
*G01N 1/22* (2006.01)
(52) U.S. Cl.
USPC ............................................................ 73/23.3
(58) Field of Classification Search
USPC ..................................... 73/23.3, 23.36, 23.21
See application file for complete search history.

(56) References Cited

U.S. PATENT DOCUMENTS

| | | | | |
|---|---|---|---|---|
| 4,818,489 | A | * | 4/1989 | Gonner et al. ................. 422/84 |
| 5,069,220 | A | * | 12/1991 | Casparie et al. .............. 600/532 |
| 2008/0139910 | A1 | * | 6/2008 | Mastrototaro et al. ........ 600/365 |

* cited by examiner

*Primary Examiner* — Daniel Larkin
*Assistant Examiner* — Jamar Ray
(74) *Attorney, Agent, or Firm* — Ladas & Parry LLP

(57) ABSTRACT

An improved method of breath sampling, particularly adapted for use in connection with motor vehicle alcohol breath monitoring devices, comprises the sending of a drive signal to a piston pump to draw a breath sample into a sensing chamber, the pump being connected to the sensing chamber. The operational status of the pump is monitored by monitoring the condition of a switch associated with the pump which is adapted to change state when the pump piston is withdrawn into its pump housing as a proper reaction of the pump to its drive signal and return to its original state when the pump piston is no longer withdrawn. The state condition of the of the switch is used to confirm proper pump operation in drawing the breath sample into the chamber; if proper pump operation is confirmed, the breath sample can be accepted for further processing and analysis.

6 Claims, 1 Drawing Sheet

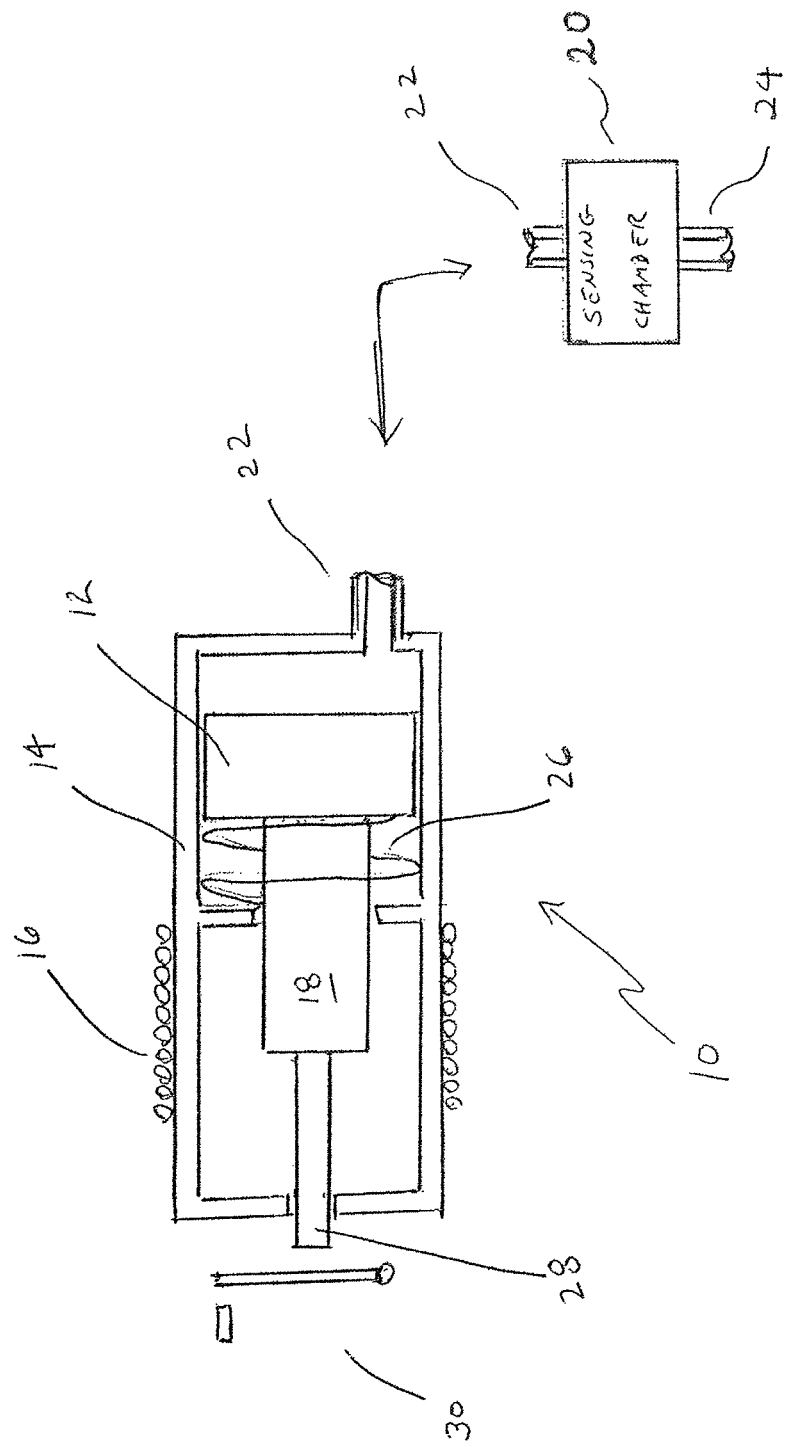

BREATH SAMPLING METHODOLOGY HAVING IMPROVED RELIABILITY

The present invention relates to breath sensing equipment and particularly such equipment that employs a sensing chamber and a pump for drawing a breath sample into the chamber.

BACKGROUND OF THE INVENTION

There is currently great interest in employing devices to curb, monitor and control the use and operation of equipment, and particularly motor vehicles, by those under the influence of alcohol. Current technology provides devices that obtain breath samples of a driver, measure the concentration of alcohol in the breath sample, correlate that concentration to a blood alcohol concentration (BAC) and use the determined value to monitor the driver's condition and control his ability to operate the vehicle. Often the sensor system is connected to an interlock for the vehicle to prevent the vehicle from being started if the BAC is over a certain level, or to issue a warning if the vehicle is already in operation.

To insure consistency of breath samples, systems often use a small pump to pull a breath sample into the sensing chamber where the alcohol concentration is measured. The pump is usually a solenoid pump, which is prone to failure. If the pump fails, a proper breath sample is not drawn into the chamber, and accordingly the output of the alcohol sensor is not an accurate reflection of the condition of the user's breath sample intended to be obtained.

It is accordingly the purpose of the present invention to provide a method of monitoring the operation of such a solenoid pump to insure proper operation and thus the proper receipt of a breath sample by the breath sampling and sensing system. A further purpose of the invention is to provide such a method that can interface with other aspects of the sensing procedure to improve the reliability and performance thereof.

BRIEF DESCRIPTION OF THE INVENTION

In accordance with the foregoing, the methodology of the present invention encompasses the use of a mechanical element, such as a pin, which is coupled to the piston of the pump that draws the breath sample into the sensing chamber. When the pump operates properly the piston retracts fully into its housing, allowing the pin to activate a switch, the condition of which indicates the status of the pump and accordingly whether a proper breath sample has been drawn into the sensing chamber. When combined with other signals derived from the drawing of a breath, such as a pressure reading, a better indication of the proper operation of the sensing system can be obtained and used to avoid inaccurate readings or attempts to foil the system.

BRIEF DESCRIPTION OF THE DRAWING

A fuller understanding of the invention will be obtained upon consideration of the following detailed description of a preferred but nonetheless illustrative embodiment thereof, when reviewed in association with the annexed drawing, wherein FIG. 1 is a diagrammatic view of a breath sensor pump coupled to a sensing chamber with which the present invention can be employed.

DETAILED DESCRIPTION OF THE INVENTION

As seen in the figure, pump 10 is of the solenoid type, with piston 12 located for reciprocating motion within housing 14. Withdrawal of the piston within the chamber is accomplished by activation of solenoid coil 16 surrounding solenoid core 18 and the housing by an appropriate electrical signal, typically controlled by the microprocessor controller for the sensing unit.

The pump's chamber is connected to sensing chamber 20 by tube 22. A second tube 24 leads from the sensing chamber to a breath sample input device, such as a hand-held mouthpiece. When the pump is activated, the core and piston retract and a breath sample is drawn into the sensing chamber from the sample input. The volume of the pump's chamber, in association with the degree of piston travel, controls the volume of the breath sample that is drawn into and through the sensing chamber, and are chosen to ensure that a sufficient breath volume is drawn for a proper analysis. In coordination with the operation of the pump an electrical sensing means in the sensing chamber measures the alcohol level of the drawn sample in accordance with known principles and methods. Once the sample is measured, power to the solenoid is cut off, the pump piston returning to the rest position through the action of return spring 26, exhausting the sample from chamber. Tubes 22 and 24 may include appropriate valuing to ensure proper breath flow.

Pin 28 is mounted to the core in a manner such that, when the pump piston is fully drawn back by solenoid action, corresponding to the successful operation of the pump to draw a breath sample into the sensing chamber, it engages switch 30, which typically has two states. The change of state resulting from engagement by or with the pin causes the switch to change state. The change of state is transmitted to the microprocessor, thus confirming to the microprocessor the proper operation of the pump. The lack of a confirming signal once an operating signal for the solenoid has issued indicates a malfunction of pump, which can be acted on as appropriate by the microprocessor. The confirmation may be affirmatively used by the microprocessor to validate the contents of the sensing chamber as a valid breath sample, allowing the sensor output to be accepted and further steps in the analysis and operation of the sensing system to proceed.

In a like manner, when return of the piston to the rest position occurs, the corresponding state change of the switch may be monitored by the microprocessor to confirm that the pump is ready to accept a new breath sample. A failure of the piston to return to the ready position maintains engagement between the pin and switch, preventing the state change required by the microprocessor.

We claim:

1. An improved method of breath sampling, comprising the steps of:
   providing a solenoid having a coil and a core coupled to a piston mounted in a housing of a piston pump;
   coupling a pin projecting outwardly from the pump housing to the solenoid core and locating a switch exterior to the pump to be activated by the pin;
   sending a drive signal to the piston pump solenoid coil to draw a breath sample into a sensing chamber, the pump having an input line connected to the sensing chamber;
   monitoring the operational status of the pump by monitoring a state of the switch, the switch being adapted to change state when contacted by the pin when the pump piston is withdrawn into its pump housing as a proper reaction of the pump to its drive signal and return to its original state when the pin ends contact with the switch when the pump piston is no longer withdrawn;
   utilizing the state of the switch to confirm proper pump operation in drawing the breath sample into the chamber;

if proper pump operation is confirmed, accepting the breath sample for further processing and analysis; and if proper pump operation is not confirmed, generating a malfunction signal.

2. The method of claim 1 wherein the switch is an electrical switch and the monitoring is performed by determining whether contacts of the switch are open or closed.

3. The method of claim 2 wherein changes of state of the switch are dictated by the state of a mechanical contact between the pump piston and the switch.

4. The method of claim 1 wherein the pump piston has an unactivated rest position, the confirmation of proper pump operation allowing further processing of the breath sample to occur and discontinuing the drive signal to allow the pump piston to withdraw to the rest position, and further comprising the steps of continuing to monitor the state of the switch after discontinuing the drive signal; and generating a malfunction signal if the state of the switch is not the original state, thus signifying that the piston has not returned to the rest position.

5. The method of claim 1 wherein upon confirmation of proper pump operation the breath sample drawn into the sensing chamber is analyzed for alcohol content, and upon completion of the analysis the drive signal to the solenoid coil is stopped to allow the pump piston to return to a non-withdrawn position, the non-withdrawn position being confirmed by a state change of the switch.

6. The method of claim 5 wherein the return of the piston to the non-withdrawn position is performed by a spring.

\* \* \* \* \*